United States Patent
Perrone (10) Patent No.: US 12,427,029 B2
(45) Date of Patent: Sep. 30, 2025

(54) FIXATION DEVICE FOR UNICONDYLAR PROSTHESIS

(71) Applicant: Howmedica Osteonics Corp., Mahwah, NJ (US)

(72) Inventor: Christine Perrone, Warwick, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 91 days.

(21) Appl. No.: 17/534,547

(22) Filed: Nov. 24, 2021

(65) Prior Publication Data

US 2022/0160512 A1     May 26, 2022

Related U.S. Application Data

(60) Provisional application No. 63/118,300, filed on Nov. 25, 2020.

(51) Int. Cl.
     *A61F 2/38*          (2006.01)
     *A61F 2/30*          (2006.01)

(52) U.S. Cl.
CPC .... *A61F 2/389* (2013.01); *A61F 2002/30224* (2013.01); *A61F 2002/30242* (2013.01); *A61F 2002/30322* (2013.01); *A61F 2002/30878* (2013.01); *A61F 2002/30884* (2013.01); *A61F 2002/30889* (2013.01); *A61F 2002/30891* (2013.01); *A61F 2002/30904* (2013.01); *A61F 2002/3895* (2013.01)

(58) Field of Classification Search
CPC ............ A61F 2/389; A61F 2002/30224; A61F 2002/30242; A61F 2002/30322; A61F 2002/30884; A61F 2002/30891; A61F 2002/30878; A61F 2002/30889; A61F 2002/3895

See application file for complete search history.

(56) References Cited

U.S. PATENT DOCUMENTS

| | | |
|---|---|---|
| 4,911,721 A | 3/1990 | Aendergaten et al. |
| 5,879,389 A | 3/1999 | Koshino |

(Continued)

FOREIGN PATENT DOCUMENTS

| | | | |
|---|---|---|---|
| EP | 2774580 A1 * | 9/2014 | ......... A61F 2/30767 |
| EP | 3593764 A1 | 1/2020 | |

(Continued)

OTHER PUBLICATIONS

Extended European Search Report issued in Appln. No. 21209759.6 mailed Apr. 19, 2022 (6 pages).

*Primary Examiner* — Megan Y Wolf
(74) *Attorney, Agent, or Firm* — Lerner David LLP (57) ABSTRACT

A tibial component includes a baseplate component that has an articular side and a bone contact side opposite the articular side. A peg extends from the bone contact side such that an acute angle is formed between a longitudinal axis of the peg and the bone contact side of the baseplate component. The peg includes a distal tip, an anterior portion, and a posterior portion. The distal tip defines a first radius of curvature, the anterior portion has a spherical portion that defines a second radius of curvature and extends from the distal tip, and the posterior portion has a conical portion that defines a taper angle relative to a longitudinal axis of the peg and extends from the distal tip.

20 Claims, 6 Drawing Sheets

(56) References Cited

U.S. PATENT DOCUMENTS

| | | |
|---|---|---|
| 6,102,951 A | 8/2000 | Sutter et al. |
| 6,102,952 A | 8/2000 | Koshino |
| 6,406,495 B1 | 6/2002 | Schoch |
| 7,462,199 B2 | 12/2008 | Justin et al. |
| 7,578,850 B2 * | 8/2009 | Kuczynski ................ A61F 2/38 623/20.21 |
| 7,862,619 B2 | 1/2011 | Clark |
| 9,345,578 B2 | 5/2016 | Collazo et al. |
| 9,381,085 B2 | 7/2016 | Axelson, Jr. et al. |
| 9,445,909 B2 | 9/2016 | Cohen et al. |
| 9,907,658 B2 | 3/2018 | Cohen et al. |
| 9,937,058 B2 | 4/2018 | Axelson, Jr. et al. |
| 10,194,963 B2 | 2/2019 | Stalcup et al. |
| 10,231,840 B2 | 3/2019 | Servidio |
| 2005/0015153 A1 | 1/2005 | Goble et al. |
| 2005/0125068 A1 | 6/2005 | Hozack et al. |
| 2012/0330429 A1 | 12/2012 | Axelson, Jr. et al. |
| 2012/0330431 A1 | 12/2012 | Rolston |
| 2013/0173010 A1 | 7/2013 | Irwin et al. |
| 2013/0218284 A1 | 8/2013 | Eickmann et al. |
| 2014/0243990 A1 * | 8/2014 | Collazo ............... A61B 17/1764 623/20.32 |
| 2014/0277548 A1 * | 9/2014 | Cohen .................... A61F 2/389 623/20.34 |
| 2016/0324649 A1 | 11/2016 | Hodorek et al. |
| 2016/0367375 A1 | 12/2016 | Boulris |
| 2017/0042690 A1 | 2/2017 | Burkhead, Jr. et al. |
| 2018/0028323 A1 * | 2/2018 | Servidio ................ A61F 2/389 |
| 2018/0092747 A1 | 4/2018 | Hopkins |
| 2020/0121465 A1 | 4/2020 | Bloebaum et al. |
| 2020/0146835 A1 | 5/2020 | Dhillon et al. |
| 2021/0000613 A1 * | 1/2021 | Schumacher ........... A61F 2/389 |
| 2022/0047394 A1 * | 2/2022 | Collins ............... A61F 2/30771 |
| 2022/0061998 A1 * | 3/2022 | Zappacosta ........... A61F 2/461 |

FOREIGN PATENT DOCUMENTS

| | | | | |
|---|---|---|---|---|
| EP | 3711714 A1 * | 9/2020 | ............ | A61B 17/157 |
| WO | WO-2012021779 A2 * | 2/2012 | ............ | A61B 17/154 |
| WO | WO-2018017615 A1 * | 1/2018 | ............ | A61F 2/4081 |

* cited by examiner

FIXATION DEVICE FOR UNICONDYLAR PROSTHESIS

CROSS-REFERENCE TO RELATED APPLICATIONS

The present application claims the benefit of the filing date of U.S. Application No. 63/118,300, filed Nov. 25, 2020, the disclosure of which is hereby incorporated herein by reference.

BACKGROUND OF THE INVENTION

Tibiofemoral joint disease is a condition commonly onset by osteoarthritis in which articular cartilage degenerates over time or is damaged through sudden trauma. This condition can result in bone-on-bone articulation which in some cases causes severe knee pain. A unicompartmental tibiofemoral joint replacement offers an alternative to a total joint replacement for patients with isolated tibiofemoral joint disease in either the lateral or medial tibiofemoral compartment, or who otherwise show no evidence of the disease present in the patellofemoral joint. In a unicompartmental tibiofemoral joint replacement, only the medial or lateral femur and tibia are replaced. This procedure provides pain relief while preserving significantly more bone than a total joint replacement.

Unicompartmental tibiofemoral joint implants have to withstand significant biomechanical forces experienced in vivo to maintain sufficient fixation. Bone cement is commonly utilized as one means of implant fixation. Bone cement is typically applied to the interface between the implant and the bone and quickly cures to form a secure bond thereby providing strong initial fixation. However, bone cement has the propensity to break down over time resulting in component loosening that may lead to sudden failure and/or the need for a revision procedure.

Biological fixation provides an alternative to bone cement. Biological fixation is often achieved through the introduction of a porous implant surface to a resected bone surface. Over time, bone grows into the porous structure resulting in securement of the implant to the bone. However, biological fixation via bone ingrowth, while providing good long-term fixation, is often inadequate for initial fixation as it takes time for the necessary bone growth to occur. In this regard, implants may deploy other features to provide initial fixation in conjunction with porous structures. Such features includes mechanical features, such as pegs, keels, and the like, which are inserted, sometimes in a press-fit manner, into the bone, which helps resist sliding or shifting of the implant relative to the bone.

Despite these available options for initial fixation, it has been found that such options are often inadequate to resist the variety of forces unicondylar tibial components are subjected to during normal use. In particular, as a femur articulates in flexion relative to a tibia, femoral condyles roll posteriorly relative to tibial condyles so that the load applied by each femoral condyle also shifts posteriorly. Such shifting load applies a moment to the implant such that an anterior end of the implant has tendency to lift off of the tibial plateau potentially pulling the aforementioned mechanical features out of the bone. Therefore, further improvements are desirable.

BRIEF SUMMARY OF THE INVENTION

In one aspect of the present disclosure, a tibial component includes a baseplate component that includes an articular side and a bone contact side opposite the articular side. The tibial component also includes a peg that extends from the bone contact side such that an acute angle is formed between a longitudinal axis of the peg and the bone contact side of the baseplate component. The peg includes a distal tip, an anterior portion, and a posterior portion. The distal tip defines a first radius of curvature. The anterior portion has a spherical portion that defines a second radius of curvature and extends from the distal tip, and the posterior portion has a conical portion that defines a taper angle relative to a longitudinal axis of the peg and that extends from the distal tip.

In another aspect of the present disclosure, a tibial component includes a baseplate component that has an articular side, a bone contact side, and anterior and posterior ends. The tibial component also includes a peg that extends from the bone contact side such that a longitudinal axis thereof is tilted at an angle relative to the articular side and toward the posterior end of the baseplate component. The peg has an anterior portion, a posterior portion and a plurality of axially extending flutes extending along its length. A first flute of the plurality of flutes is disposed within the posterior portion and has an interrupted edge that defines a plurality of teeth arrayed along its length, and a second flute disposed within the anterior portion and has a continuous edge extending along the length thereof.

In a further aspect of the present disclosure, a tibial component includes a baseplate component that has an articular side, a bone contact side, and anterior and posterior ends. A peg extends from the bone contact side and has a distal tip that defines a first radius of curvature, a spherical portion that extends from the distal tip and defines a second radius of curvature, a conical portion that extends from the distal tip and defines a taper angle relative to a longitudinal axis of the peg, and a cylindrical portion that extends from the spherical portion and conical portion to the baseplate component.

BRIEF DESCRIPTION OF THE DRAWINGS

The features, aspects, and advantages of the present invention will become better understood with regard to the following description, appended claims, and accompanying drawings in which:

DETAILED DESCRIPTION

When referring to specific directions in the following discussion of certain implantable devices, it should be understood that such directions are described with regard to the implantable device's orientation and position during exemplary application to the human body. Thus, as used herein, the term "proximal" means close to the heart and the term "distal" means more distant from the heart. The term "inferior" means toward the feet and the term "superior" means toward the head. The term "anterior" means toward the front of the body or the face, and the term "posterior" means toward the back of the body. The term "medial" means toward the midline of the body, and the term "lateral" means away from the midline of the body. Also, as used herein, the terms "about," "generally" and "substantially" are intended to mean that slight deviations from absolute are included within the scope of the term so modified.

Figure 1A:
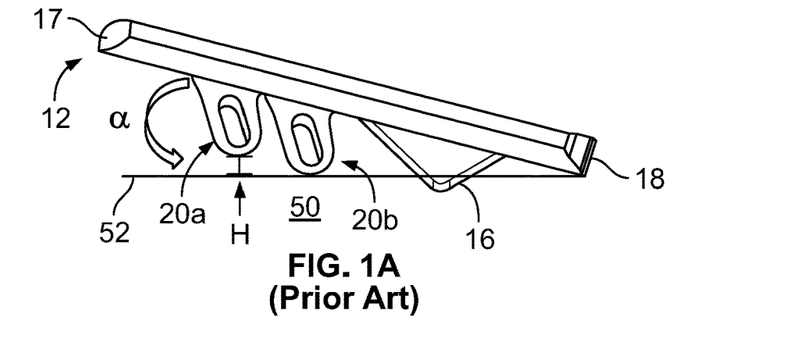
FIGS. 1A-1D illustrate a prior art unicondylar tibial component and implantation thereof into a tibia.
Figure 1B:
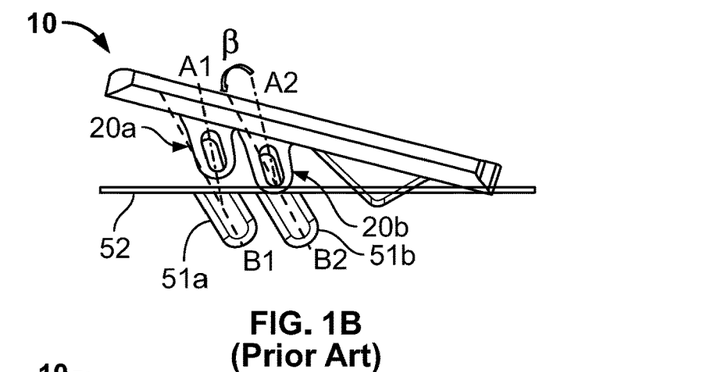
Figure 1C:
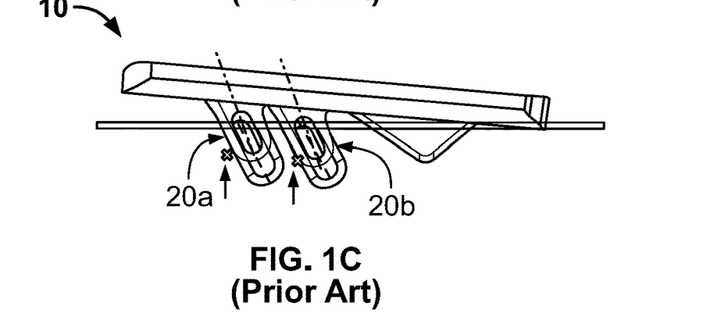
Figure 1D:
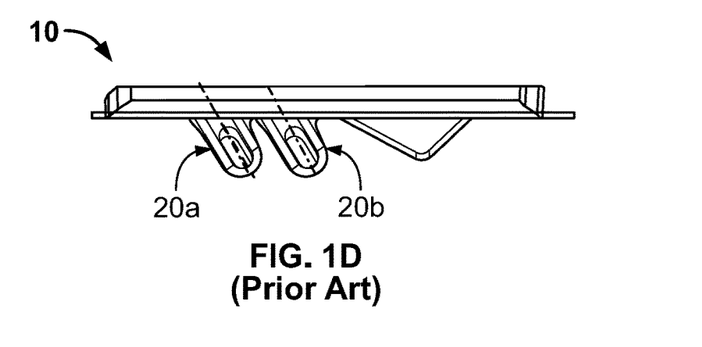

FIGS. 1A-1D depict a prior art unicondylar tibial component 10 and its implantation onto bone 50. Tibial component 10 includes a baseplate 12, keel 16, and first and second pegs 20a-b. Pegs 20a-b and keel 16 extend from baseplate 12. In a surgical procedure, a posterior end 18 of baseplate 12 is rested on a prepared bone surface 52, the second peg 20b is positioned adjacent bone surface 52, and first peg 20a is positioned above bone surface 52 a height H such that baseplate 12 is oriented at an implantation angle α. The longitudinal axes A1, A2 of first and second pegs 20a-b are angled relative to longitudinal axes B1, B2 of corresponding prepared bone holes 51a-b by an angle β which decreases and converges to zero as pegs 20a-b are inserted into bone 50. From this position, anterior end 17 of baseplate 12 is rotated about posterior end 18 so as to insert pegs 20a-b into the previously prepared bone holes 51a-b and keel 16 into bone 50. As can be seen in FIG. 1C, as pegs 20a-b are inserted into bone holes 20a-b, the ends of each peg 20a-b, due to the non-zero β angle and structure of each peg 20a-b, impact the wall of the corresponding bone hole 50a-b prior to being fully inserted and aligned as in FIG. 1D. Pegs 20a-b are generally cemented into bone. In this regard, the preparation for traditional bullet tip pegs, such as pegs 20a-b, tend to be deeper than the implant design so that the component can be fully inserted into the bone 50 along with bone cement.

FIGS. 2A-2D depict a unicondylar tibial component 100 according to an embodiment of the present disclosure. Tibial component 100 generally includes a baseplate 112, keel 130, first peg 120a, and second peg 120b.

Figure 2A:
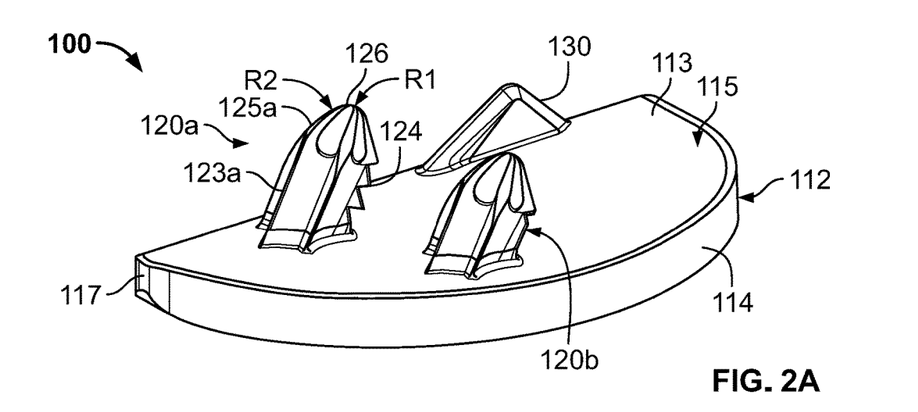
FIG. 2A is a bottom perspective view of a unicondylar tibial component according to an embodiment of the present disclosure.

Baseplate 112 has an articular side or superior side 111 and a bone contact side or inferior side 115. Articular side 111 is configured to receive a tibial insert 140 as known in the art. Since tibial component 100 is a unicondylar component, such tibial insert 140 may include a single condyle for articulation with a corresponding condyle of a femoral component. Bone contact side 115, in the depicted embodiment, includes a porous bone contact surface 113. Such porous surface 113 has a porous structure configured to promote bone ingrowth therein for biological fixation. As shown, baseplate 112 has an anterior end 117 and a posterior end 118. A sidewall 114 that defines a thickness of baseplate 112 extends between anterior and posterior ends 117, 118 and between articular and bone contact sides 111, 115.

Keel 130 extends from bone contact side 115 of baseplate 112 and is a fin-like structure that is triangular in shape. In the embodiment depicted, keel 130 is positioned nearer to posterior end 118 than anterior end 117. Keel 130 is also oriented in an anteroposterior direction so that its narrowest cross-sectional dimension is transverse to the anteroposterior direction. Keel 130 also may include a porous structure for bone ingrowth and may be press-fit into bone 150 and be self-broaching such that the bone 150 does not need to be resected prior to its insertion.

Figure 2B:
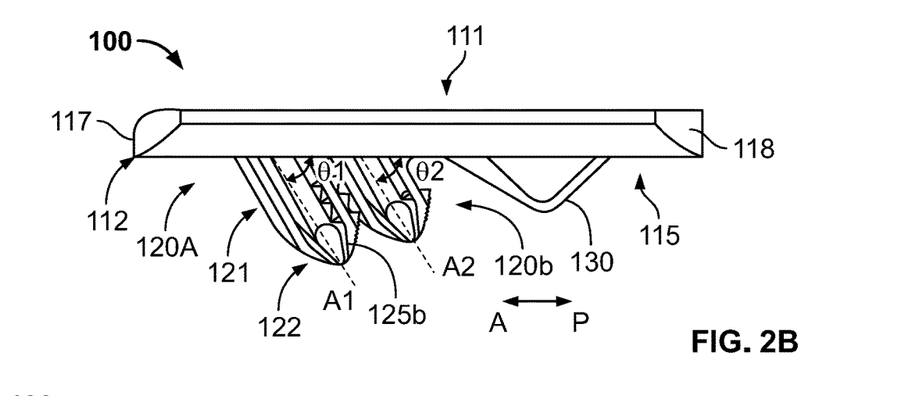
FIG. 2B is a side view of the unicondylar tibial component of FIG. 2A.

Tibial component 100 includes a first peg or anterior peg 120a and a second peg or posterior peg 120b. While tibial component 100 includes two pegs 120a-b, tibial component 100 can include more or less pegs 120 as desired. First and second pegs 120a-b each extend from bone contact side 115 of baseplate 112 such that the longitudinal axes thereof A1, A2 each form an acute angle θ1, θ2 with bone contact side 115, as best shown in FIG. 2B. In this regard, pegs 120a-b, along with their longitudinal axes A1, A2, are tilted or angled posteriorly so that they generally extend in the posterior direction toward posterior end 118 of baseplate 112. In the embodiment depicted, θ1 and θ2 are each 60 degrees. However, θ1 and θ2 may be 40 to 80 degrees.

Figure 3A:
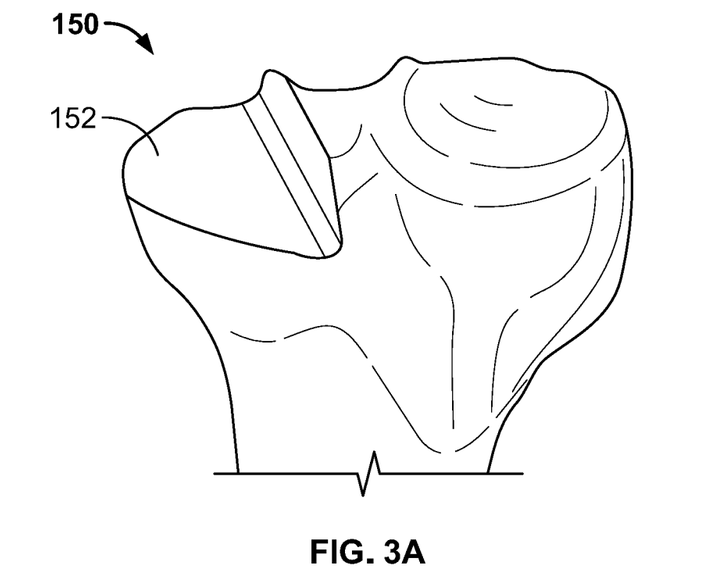
FIGS. 3A-3F illustrates a method of implanting the unicondylar tibial component of FIG. 2A.
Figure 3B:
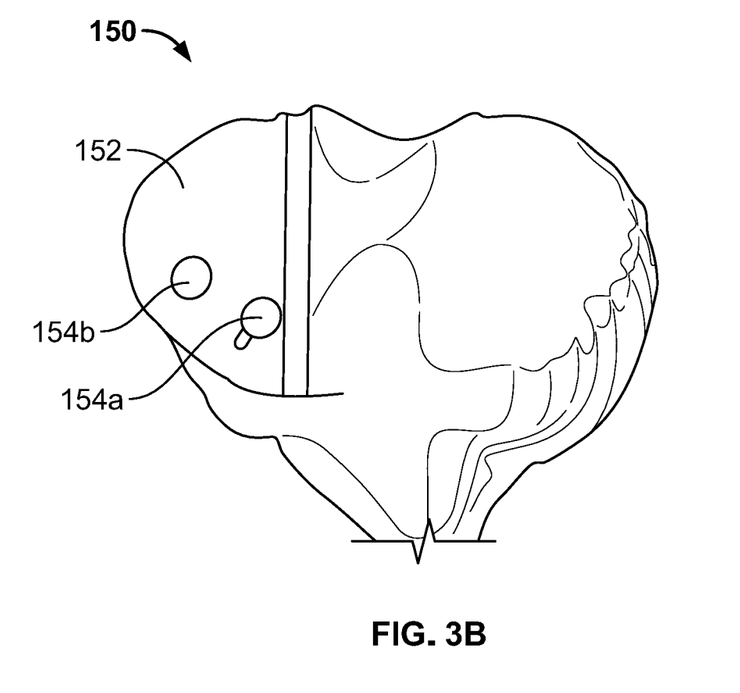
Figure 3C:
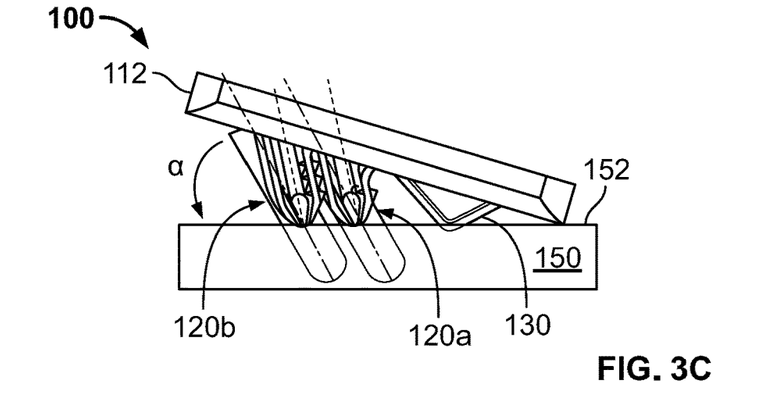

First peg 120a is positioned anterior of second peg 120b and keel 130. Second peg 120b is positioned between keel 130 and first peg 120a in the anteroposterior direction, as best shown in FIG. 2B. However, first peg 120a is positioned between second peg 120b and keel 130 in the lateral-medial direction, as best shown in FIG. 2A. First peg 120a also has a length that is longer than second peg 120b. As shown in FIG. 3C, discussed further below, this extended length allows first peg 120a to be positioned adjacent to bone 150, rather than above it, when positioned relative to a bone surface 152 at angle α, which is the same angle α described above. This allows first peg 120a to be impacted into unprepared bone (i.e., bone without a predrill bone hole) or inserted into a prepared bone hole at the same time as second peg 120b. In addition, this extended length provides enhanced fixation.

Figure 2C:
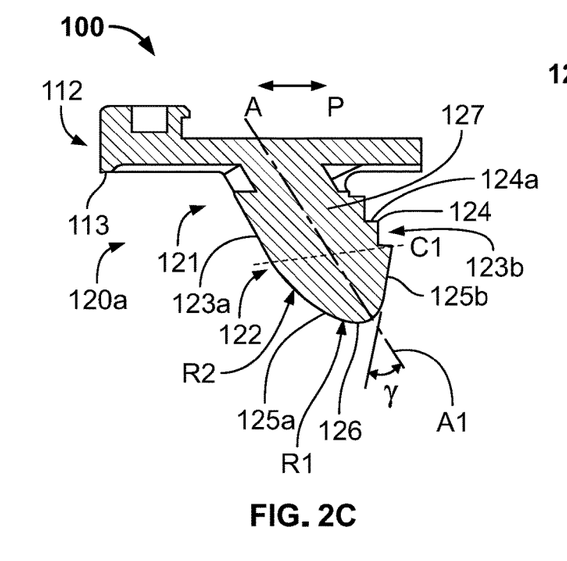
FIG. 2C is a sectional view of an anterior peg of the unicondylar tibial component of FIG. 2A.

First peg 120a has an anterior portion, posterior portion, proximal portion 121, and distal portion 122. Anterior portion and posterior portion are separated by a plane that extends in a lateral medial direction through first peg and is coplanar with longitudinal axis A1. The proximal and distal portions are separated by a plane Cl extending transverse to axis A1, as shown in FIG. 2C.

A plurality of flutes or ridges 123 extend along the length of peg 120a from a distal tip 126 thereof to baseplate 115. Such flutes 123 define relief channels 129 therebetween. Flutes 123 are configured to cut into prepared or unprepared bone so as to compress bone within the relief channels 129 to enhance press-fit fixation. In this regard, pegs 120a-b may be self-broaching such that they can cut through bone on their own and form a bone hole around such pegs 120a-b. Flutes 129 each have an outer edge 128 which defines a peripheral shape of peg 120a. Such outer edge 128 may taper so that its thickness increases in a distal to proximal direction so as to further increase compression of the bone along the length of flutes 123.

Distal portion 122 of peg 120a incudes distal tip 126, a spherical portion or rounded portion 125a, and a conical portion 125b. Spherical portion 125a extends from distal tip 126 and is disposed at the anterior portion of peg 120a, as shown in FIG. 2C. Conical portion 125b also extends from distal tip 126 and is disposed at the posterior portion of peg 120a. Distal tip 126 is rounded such that it has a first radius of curvature R1. Spherical portion 125a is rounded such that it has a second radius of curvature R2. R2 is greater than R1. In the embodiment depicted, R2 is 12 mm and R1 is 2 mm.

However, R1 can be 0 mm to 4.25 mm, and R2 can be 4.25 mm to 20 mm. Conical portion 125a and longitudinal axis A1 define a taper angle γ. In the embodiment depicted, γ is 40 degrees but may be 10 degrees to 60 degrees. Distal tip 126, as shown, is noticeably sharper than that of pegs 20a-b. This allows pegs 120a-b to penetrate bone without the need for a preformed bone hole such that pegs 120a-b are self-broaching.

Proximal portion 121 is generally cylindrical and extends from baseplate 112 to distal portion 122. In this regard, proximal portion 121 extends from both spherical portion 125a and conical portion 125b. At least one flute 123 is a jagged or toothed flute 123b. Such flute 123b has an interrupted outer edge 123 so as to form a plurality of teeth 124 arrayed along a length of such flute 123b where such teeth 124 are disposed within the proximal portion 121 and posterior portion of peg 120a. Teeth 124 are configured such that a flat 124a of teeth 124 are parallel to surface 113 so that, when fully seated, teeth 124 provide the maximum resistance to pull-out. Thus, the flats of teeth 124 can be configured so as to not be parallel, but such configurations would not be optimal. Additionally, at least one flute 123 is a continuous or uninterrupted flute 123a. Such flute 123a has continuous outer edge (i.e., no teeth) extending along its entire length including the proximal portion 121 and anterior portion of peg 120a. More particularly, peg 120a has a plurality of flutes 123b with teeth 124 that are disposed within the posterior portion thereof, and a plurality of flutes 123a without teeth 124 disposed within the anterior portion of peg 120a. The teeth 124 of flutes 123b at the posterior portion of peg 120a allows such teeth 124 to dig into bone to resist pull-out and consequently lift-off of tibial component 100. The flutes 123a with no teeth 124 at the anterior portion allows for ease of insertion into the bone. Moreover, as described further below, the radiused, spherical portion 125a provides relief to minimize impingement on the bone as peg 120a is inserted which also allows first peg 120a to be longer than second peg 120b. Although first peg 120a is longer than second peg 120b, second peg 120 has the same configuration as just described.

It is advantageous to have minimal disruption to bone preparation to ensure maximum press-fit between the component fixation features, such as pegs 120a-b and keel 130, and bone for cementless component implantation. As placement and balancing methods improve in the industry, there is a desire to eliminate trialing steps. Trials in knee replacement, and in particular unicompartmental knee replacement, often mimic the fixation features of the implant and have a tendency to expand the bone preparation thereby potentially weakening the press-fit of the final implant. The keel 130 and pegs 120a-b are designed to be self-broaching to allow a surgeon to eliminate trialing prior to implantation of implant 100 which would minimize disturbances to the press-fit of implant 100 and reduce operating times.

Figure 2D:
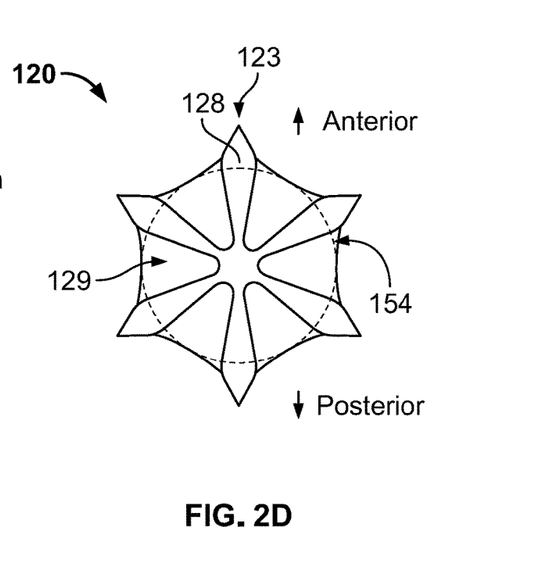
FIG. 2D is a bottom view fixation pegs of the unicondylar tibial component of FIG. 2A.
Figure 3D:
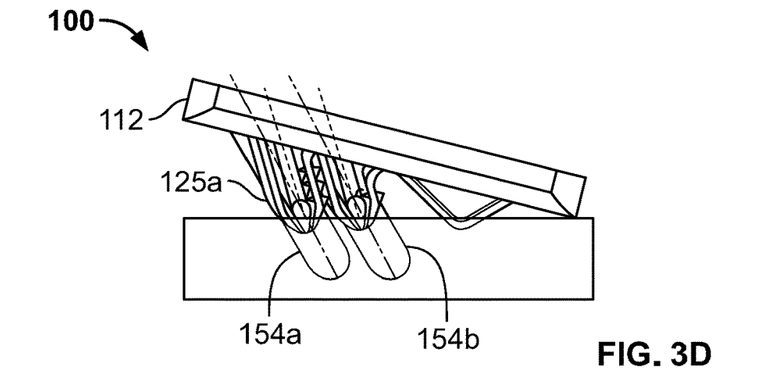
Figure 3E:
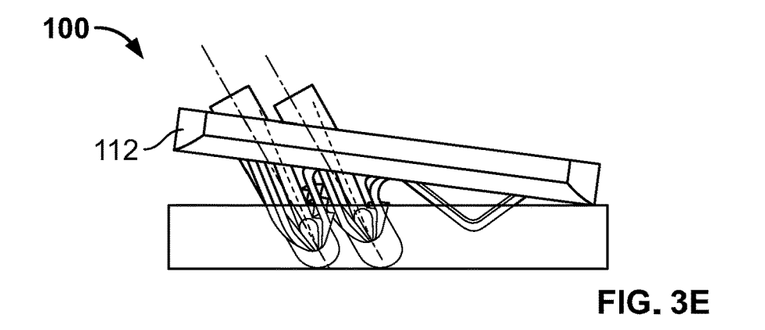
Figure 3F:
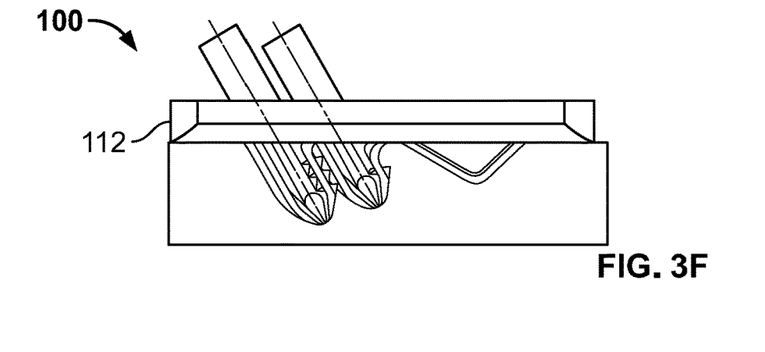

FIGS. 3A-3F depict a method implanting tibial component 100. Such method may be performed manually or robotically assisted. A tibia 150 is first resected so as to remove either a medial or lateral condyle thereof to expose a resected surface 152. Bone holes 154a-b may be formed for first and second pegs 120a-b. However, in some procedures, bone holes 154a-b may not be pre-formed and may instead be formed by the pegs 120a-b themselves. Posterior end 118 of baseplate 112 is rested on the prepared bone surface 152 at angle α. In this position, first and second pegs 120a-b are positioned adjacent to the bone surface 152 and just above bone holes 154a-b. The longitudinal axes A1, A2 of first and second pegs 125a-b are angled relative to longitudinal axes B1, B2. From this position, anterior end 117 of baseplate 112 is rotated about posterior end 118 so as to insert pegs 120a-b into the previously prepared bone holes 154a-b and keel 130 into bone 150. FIG. 2D depicts a perimeter of a bone hole relative to one of the pegs. As illustrated, the major diameter and minor diameter of peg 120 are greater than a diameter of a bone hole 154. In this regard, as pegs 120a-b are inserted into the bone 150, the flutes 123a-b cut into the bone hole wall and the minor diameter of the proximal portion 121 of pegs 120a-b presses against the bone wall to form a press-fit along flutes 125a-b and along the shank 127 of pegs 120a-b. Additionally, as illustrated in FIGS. 3D and 3E, the curvature of spherical portion 125a slides along the bone wall so as to minimally disrupt the bone forming the bone hole wall. Once the pegs 120a-b are fully seated, as shown in FIG. 3F, teeth 124 of flutes 123b dig into the bone to further help prevent lift-off of tibial component 100.

Figure 4:
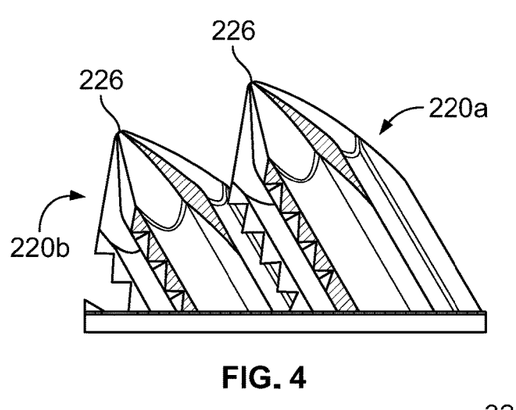
FIG. 4 is an enhanced view of fixation pegs of a unicondylar tibial component according to another embodiment of the present disclosure.
Figure 5:
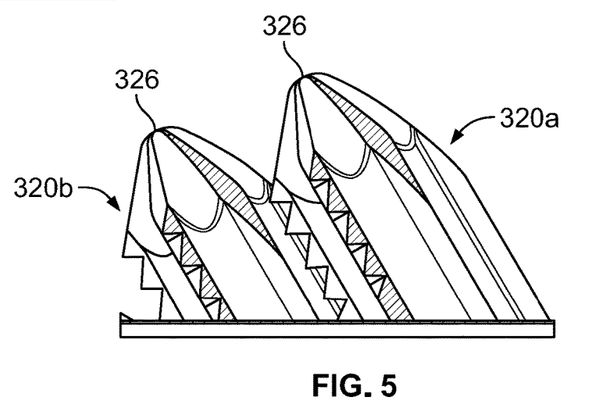
FIG. 5 is an enhanced view of fixation pegs of a unicondylar tibial component according to a further embodiment of the present disclosure.
Figure 6:
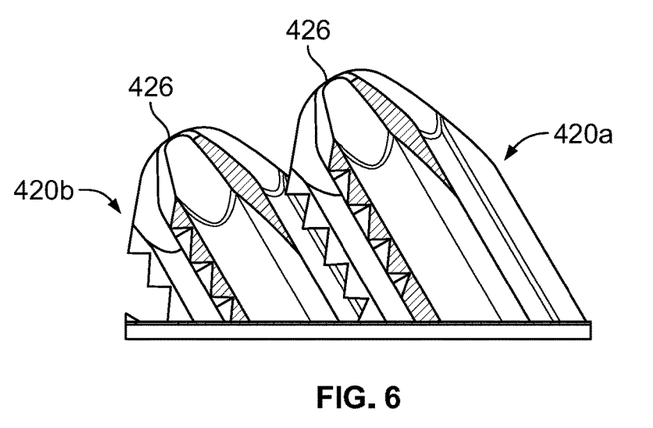
FIG. 6 is an enhanced view of fixation pegs of a unicondylar tibial component according to yet another embodiment of the present disclosure.
Figure 7:
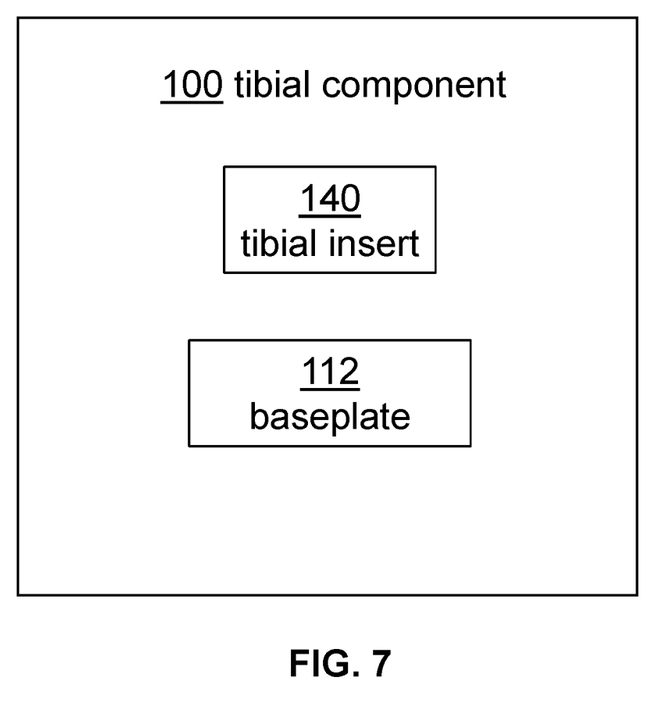
FIG. 7 is a schematic view of a tibial component according to an embodiment of the disclosure.

FIGS. 4-6 depict alternative peg embodiments that may be implemented in a tibial component. For ease of review, like elements will be accorded like reference numerals to that of component 100, but within the 200, 300, and 400 series of numbers. For instance, pegs 220a-b, 320a-b, and 420a-b include all of the same features previously described with respect to pegs 120a-b. However, pegs 220a-b, 320a-b, and 420a-b each have a differing level of sharpness to their respective distal tips 226, 326, and 426. In other words, the radius of curvatures of distal tips 226, 326, and 426 differ such that pegs 220a-b have the sharpest distal tips 226 while pegs 420a-b have the bluntest distal tips 426. In this regard, a radius of 0 mm to 4.25 mm correlates to the sharpest tip to the dullest tip. The sharpness of such tips 226, 326, 426 may be selected depending on whether or not a bone hole has been pre-formed and the quality of the bone.

Although the foregoing description has been directed to unicondylar tibial prostheses, it should be understood that the inventive concepts herein can also be applied to tibial components for total knee arthroplasty ("TKA"). TKA tibial components generally have two condyles, a medial and lateral condyle, rather than a singular condyle as in the case of a unicondylar tibial component. However, such TKA tibial components include baseplates from which one or more of the aforementioned pegs can extend.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tibial component, comprising:
    a baseplate component having an articular side and a bone contact side opposite the articular side; and
    a peg extending from the bone contact side such that an acute angle is formed between a longitudinal axis of the peg and the bone contact side of the baseplate component, the peg having, an anterior portion, a posterior portion opposite the anterior portion, a distal tip distal to the anterior and posterior portions and a plurality of flutes extending from the bone contact side to the distal tip, a first surface of the distal tip defining a first radius of curvature, a second surface of the anterior portion being spherical and defining a second radius of curvature different from the first radius of curvature, the second surface extending from the first surface of the distal tip, and a third surface of the posterior portion being conical and defining a taper angle relative to a longitudinal axis of the peg, the third surface extending from the first surface of the distal tip.

2. The tibial component of claim 1, wherein the longitudinal axis of the peg extends from the baseplate component in an anterior to posterior direction.

3. The tibial component of claim 1, wherein the acute angle is 40 degrees to 80 degrees.

4. The tibial component of claim 1, wherein the taper angle is 10 degrees to 60 degrees.

5. The tibial component of claim 1, wherein the first radius of curvature is smaller than the second radius of curvature.

6. The tibial component of claim 5, wherein the first radius of curvature is 0 mm to 4.25 mm, and the second radius of curvature is 4.24 mm to 20 mm.

7. The tibial component of claim 1, further comprising a keel extending from the bone contact side of the baseplate component.

8. The tibial component of claim 1, wherein a first flute disposed within the posterior portion has an interrupted edge defining a plurality of teeth, and a second flute disposed within the anterior portion has a continuous edge extending along its length.

9. The tibial component of claim 1, wherein the peg has a proximal portion and a distal portion, the proximal portion being cylindrical and extending from the baseplate component to the distal portion, the distal portion having the distal tip, spherical portion, and conical portion.

10. The tibial component of claim 1, wherein the tibial component is a unicondylar tibial component which includes a tibial baseplate and a tibial insert, the tibial insert being connectable to the tibial baseplate and having an articular surface.

11. The tibial component of claim 1, wherein a portion of the first surface in a first plane has the first radius of curvature and a portion of the third surface in the first plane is linear.

12. A tibial component, comprising:
a baseplate component having an articular side, a bone contact side, and anterior and posterior ends; and
a peg extending from the bone contact side such that a longitudinal axis thereof is tilted at an angle relative to the articular side and the peg extends from the bone contact side toward the posterior end of the baseplate component, the peg having an anterior portion, a posterior portion opposite the anterior portion and a plurality of axially extending flutes extending along a length of the peg from the bone contact side to a distal end of the peg remote from the bone contact side, a first flute of the plurality of axially extending flutes being disposed within the posterior portion and having an interrupted edge defining a plurality of teeth arrayed along a part of the first flute that is less than an entire length of the first flute, and a plurality of anterior flutes of the plurality of axially extending flutes being disposed within the anterior portion, each of such plurality of anterior flutes having a continuous edge extending along an entire length thereof,
wherein the plurality of anterior flutes are spaced apart by relief channels such that an entirety of the anterior portion is encompassed by the plurality of anterior flutes and the relief channels.

13. The tibial component of claim 12, wherein the peg includes a distal tip and a spherical portion and conical portion extending therefrom.

14. The tibial component of claim 13, wherein the spherical portion is disposed within the anterior portion and the conical portion is disposed within the posterior portion.

15. The tibial component of claim 14, wherein the spherical and conical portions are defined by edges of the flutes.

16. The tibial component of claim 13, wherein the distal tip has a first radius of curvature, and the spherical portion has a second radius of curvature greater than the first radius of curvature.

17. The tibial component of claim 13, wherein the peg has a proximal portion and a distal portion, the proximal portion having a cylindrical portion extending from the baseplate component to the distal portion, the distal portion having the distal tip, spherical portion, and conical portion.

18. The tibial component of claim 12, further comprising another peg extending from the bone contact side of the baseplate component.

19. A tibial component, comprising:
a baseplate component having an articular side, a bone contact side, and anterior and posterior ends; and
a peg extending from the bone contact side having a distal tip defining a first radius of curvature, a spherical portion extending from the distal tip toward the baseplate component and defining a second radius of curvature different from the first radius of curvature, a conical portion extending from the distal tip opposite the spherical portion and defining a taper angle relative to a longitudinal axis of the peg, a cylindrical portion extending from the spherical portion and conical portion to the baseplate component, and a plurality of flutes extending from the bone contact side to the distal tip.

20. The tibial component of claim 19, wherein the portion includes a plurality of flutes extending along a length thereof, and at least one of but not all of the plurality of flutes have a series of teeth along an edge thereof.

* * * * *